(12) United States Patent
Sun et al.

(10) Patent No.: US 8,519,002 B2
(45) Date of Patent: *Aug. 27, 2013

(54) COLCHICINE SOLID COMPLEX; METHODS OF MAKING; AND METHODS OF USE THEREOF

(75) Inventors: Tong Sun, Marlton, NJ (US); David Jonaitis, Brookston, IN (US); Stephan D. Parent, West Lafayette, IN (US)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 146 days.

This patent is subject to a terminal disclaimer.

(21) Appl. No.: 13/158,512

(22) Filed: Jun. 13, 2011

(65) Prior Publication Data

US 2011/0245336 A1    Oct. 6, 2011

Related U.S. Application Data

(63) Continuation of application No. 12/416,990, filed on Apr. 2, 2009, now Pat. No. 8,003,700.

(60) Provisional application No. 61/042,897, filed on Apr. 7, 2008.

(51) Int. Cl.
*C07C 225/20* (2006.01)

(52) U.S. Cl.
USPC ......................................................... 514/629

(58) Field of Classification Search
USPC ......................................................... 514/629
See application file for complete search history.

(56) References Cited

U.S. PATENT DOCUMENTS

| 3,329,694 A | 7/1967 | Martel et al. |
| 8,003,700 B2 | 8/2011 | Sun et al. |
| 2005/0181041 A1 | 8/2005 | Goldman |

FOREIGN PATENT DOCUMENTS

| WO | 2004078163 A2 | 9/2004 |
| WO | 2004078163 A3 | 9/2004 |
| WO | 2005055983 A2 | 6/2005 |
| WO | 2007019255 | 2/2007 |
| WO | 2007146715 | 12/2007 |
| WO | 2009126513 A1 | 10/2009 |

OTHER PUBLICATIONS

European Search Report for European Application No. 09730714.4 European Filing Date Apr. 3, 2009, Date of Report Jun. 6, 2012, 5 pages.
Niel et al., "Colchicine Today", Joint Bone Spine 73, 2006, pp. 672-678.
27650 Colchicine BioChemika, >96.0% (HPLC), 27650 Colchicine, http://www.sigmaaldrich.com/catalog/search/ProductDetail/FLUKA/27650?PrtPrv=1&I, Oct. 31, 2007, 4pages.
Byrn et al., Pharmaceutical Solids: A Strategic Approach to Regulatory Considerations, Pharmaceutical Research, vol. 12, No. 7, 1995, 945-954.
C9754 Colchicine~ 95% (HPLC), powder, http://www.sigmaaldrich.com/catalog/search/ProductDetail/SIGMA/C9754.
Colchicine, European Pharmacopeia 5.0, Jan. 2005, 1357-1359.
Davies, Changing the Salt, Changing the Drug, Pharm. J. 266 (2001), p. 322-323.
The Merck Index, 13th Edition, 2496, Colchicine, 2001, 3 pages.
USP 27, Colchicine, Official Monographs, Jan. 2004, 507-508.

(Continued)

*Primary Examiner* — Paul Zarek
(74) *Attorney, Agent, or Firm* — Cantor Colburn LLP

(57) ABSTRACT

Disclosed are new colchicine solid complexes, methods of making the solid complexes as well as formulations prepared therefrom and uses thereof.

18 Claims, 7 Drawing Sheets

(56) References Cited

OTHER PUBLICATIONS

International Search Report; International Application No. PCT/US2009/039376; International Filing Date Apr. 3, 2009; 4 pages.

Written Opinion of the International Searching Authority; International Application No. PCT/US2009/039376; International Filing Date Apr. 3, 2009; 4 pages.

Bagnato et al., "Synthesis and Characterization of a Cobalamin-Colchicine Conjugate as a Novel Tumor-Targeted Cytotoxin." Journal of Organic Chemistry, 2004, vol. 69, No. 26, pp. 8987-8996. Abstract Only (1 page).

Nakagawa-Goto, K. et al., "Antitumor Agents. Part 236: Synthesis of Water-Soluble Colchicine Derivatives". Bioorganic & Medicinal Chemistry Letters, 2005, vol. 15, pp. 235-238. Abstract Only (1 page).

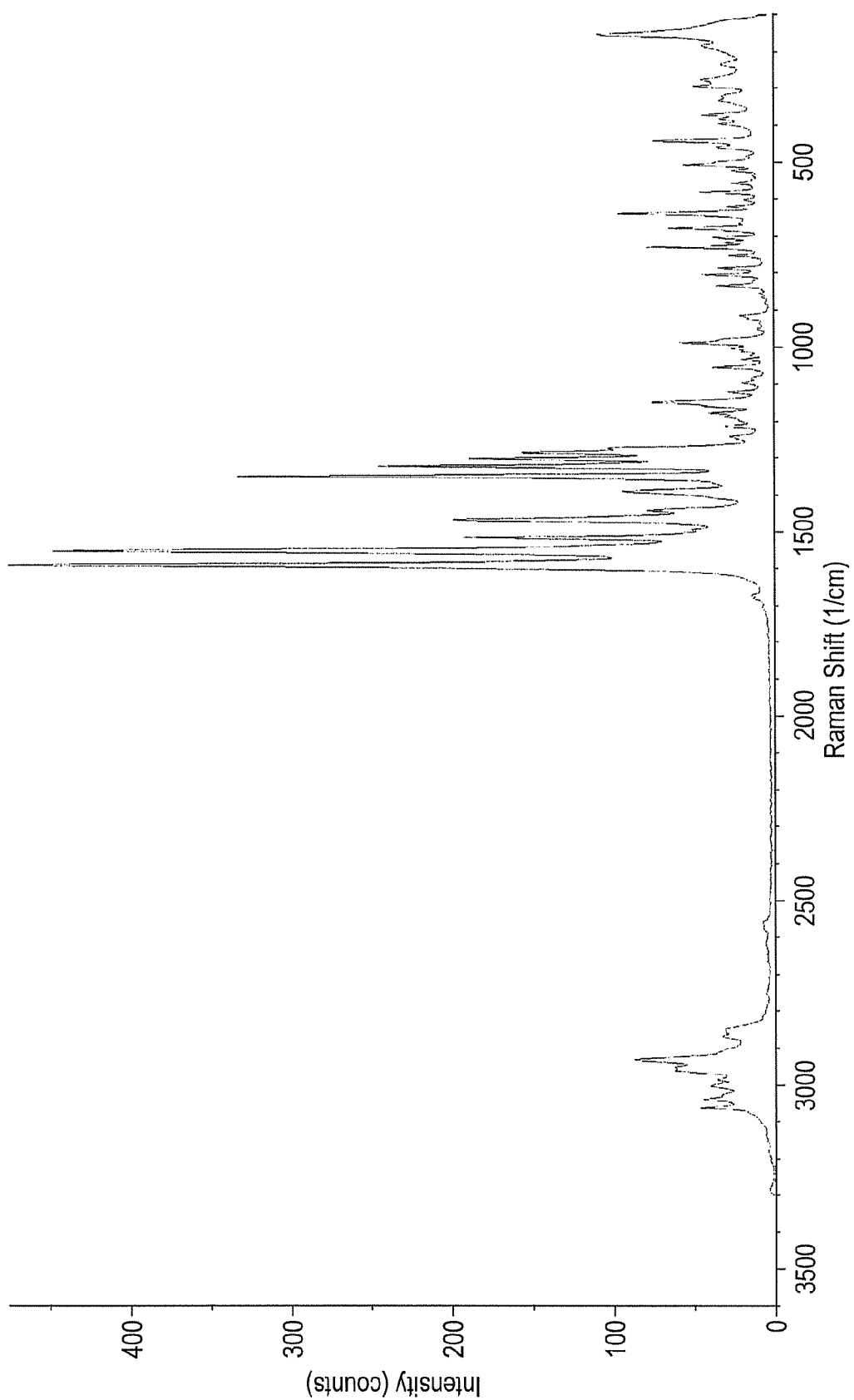

COLCHICINE SOLID COMPLEX; METHODS OF MAKING; AND METHODS OF USE THEREOF

CROSS REFERENCE TO RELATED APPLICATION

This application is a continuation of prior application Ser. No. 12/416,990 filed Apr. 2, 2009, which claims the benefit of U.S. Provisional Application Ser. No. 61/042,897 filed Apr. 7, 2008, each of which is hereby incorporated by reference in its entirety.

BACKGROUND

Colchicine, chemical name (−)-N-[(7S,12aS)-1,2,3,10-tetramethoxy-9-oxo-5,6,7,9-tetrahydrobenzo[a]heptalen-7-yl]-acetamide, (N-((7S)-5,6,7,9-tetrahydro-1,2,3,10-tetramethoxy-9-oxobenzo[a]heptalen-7-yl)-acetamide, IUPAC), CAS Registry No. 64-86-8 is a known gout suppressant.

Different crystalline forms, non-crystalline forms, hydrates and solvates of an active agent can exhibit vastly different physical properties such as solubility, melting point, hardness, optical properties, dissolution, and the like. These differences such as varying dissolution can result in differences in the therapeutic activity. A thorough understanding of the various crystalline forms, non-crystalline forms, hydrates and solvates of an active agent is an important consideration in formulating the active agent, specifically when trying to achieve consistency of any resulting pharmaceutical product batch to batch.

There remains a need in the art for new solid forms of colchicine having improved properties of solubility, stability, processability and the like.

SUMMARY

In one embodiment, a solid complex comprises colchicine and a guest, wherein the guest is malic acid, oxalic acid, or para-toluenesulfonic acid.

In another embodiment, a composition comprises a solid complex comprising colchicine and a guest, wherein the guest is malic acid, oxalic acid or para-toluenesulfonic acid; and a pharmaceutically acceptable excipient.

In yet another embodiment, a method of preparing a solid complex comprises slurrying a combination of colchicine, L-malic acid, and ethyl acetate to form colchicine malic acid co-crystal.

In still yet another embodiment, a method of preparing a solid complex comprises preparing colchicine malic acid co-crystal by vapor diffusion of hexanes into an ethyl acetate solution containing equimolar amounts of colchicine and L-malic acid.

In yet another embodiment, a method of preparing a solid complex comprises crystallizing colchicine oxalic acid co-crystal from a solution of acetonitrile and diethyl ether.

In one embodiment, a method of preparing a solid complex comprises crystallizing colchicine para-toluenesulfonic acid co-crystal from a solution of tetrahydrofuran and hexanes.

These and other embodiments, advantages and features of the present invention become clear when detailed description and examples are provided in subsequent sections.

BRIEF DESCRIPTION OF DRAWINGS

FIG. 7 illustrates a FT-Raman spectrum of colchicine para-toluenesulfonic acid co-crystal.

DETAILED DESCRIPTION

Figure 1:
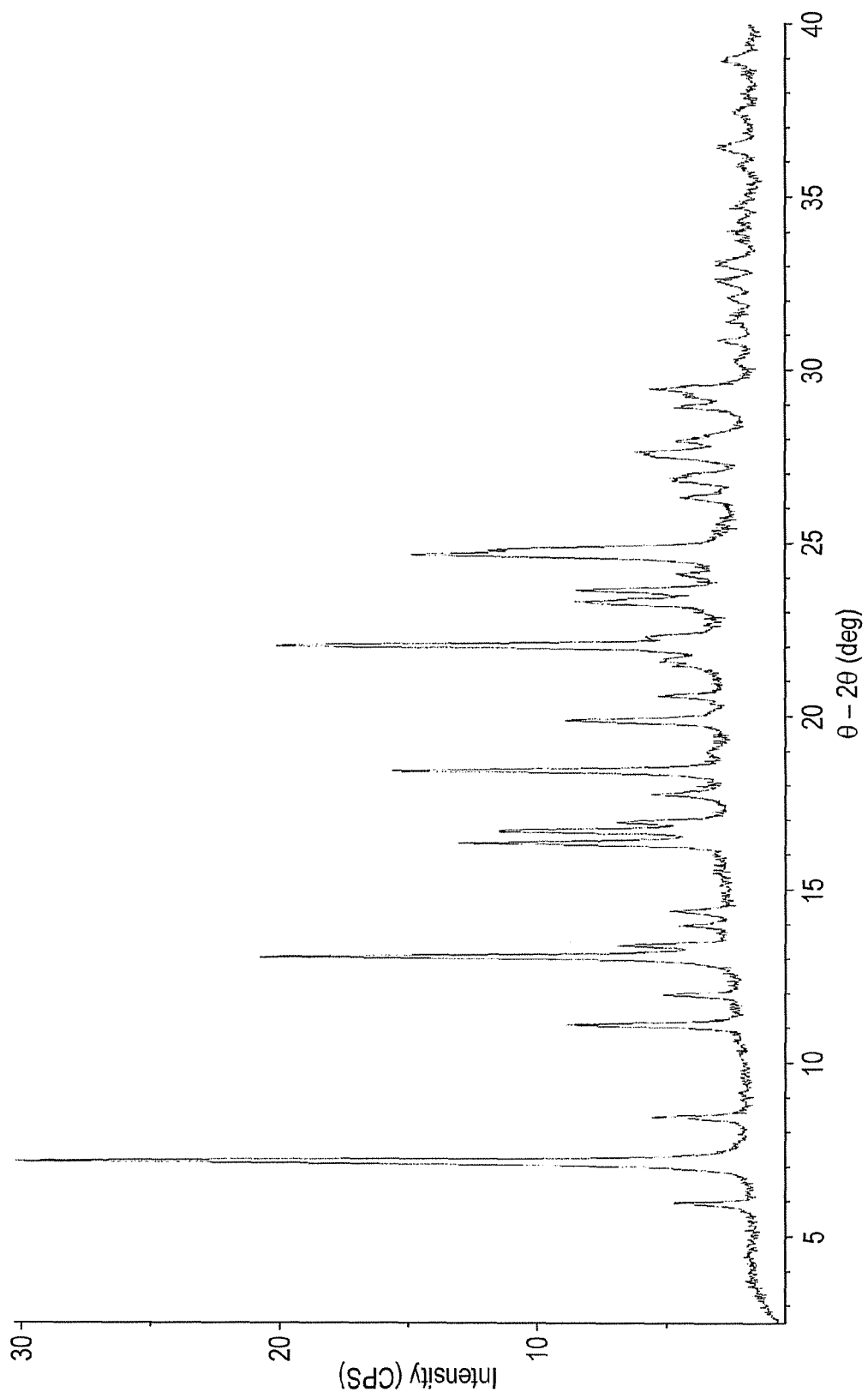
FIG. 1 illustrates an XRPD pattern of colchicine malic acid co-crystal.

Disclosed herein are novel colchicine solid complexes, methods of preparing the solid complexes, compositions prepared therefrom, and uses thereof. It has been unexpectedly discovered herein that colchicine can exists as a solid complex (e.g., a co-crystal) with different guest molecules. Novel solid complexes disclosed herein include colchicine malic acid co-crystal, colchicine oxalic acid co-crystal, colchicine oxalic acid co-crystal tetrahydrofuran solvate, and colchicine para-toluenesulfonic acid co-crystal.

"Solid complex" means a solid form containing colchicine and an additional component ("guest") which interact with one another to result in a solid material having a different physicochemical property than the corresponding free colchicine. The interactions between the colchicine and the guest can be hydrogen bonding, van der Waals interactions, electrostatic interactions, hydrophobic interactions, ionic interactions, a combination thereof, and the like. Exemplary solid complexes include co-crystals (i.e. a crystalline supramolecular complex), single phase molecular dispersions, and the like. The properties can include solubility, melting point, spectroscopic, etc.

The solid complex may include one or more solvate or water molecules in the crystalline lattice (e.g., solvates or hydrates of co-crystals, or a co-crystal further comprising a solvent or water molecule).

"Colchicine" is inclusive of all crystalline forms including all polymorphs, non-crystalline forms, anhydrous forms, hydrates, and solvates unless specifically indicated otherwise.

"Guest" means an organic acid, specifically malic acid, oxalic acid, and para-toluenesulfonic acid.

The ratio of colchicine to guest may be for example, 1:1, 1:1.5, and 1:2. In certain embodiments, the ratio is 1:1, 1:2, 1:3, 1:4, 1:5, 1:6, 1:7, 1:8, 1:9, or 1:10 colchicine to guest. In other embodiments, the ratio is 1:1, 1:2, 1:3, 1:4, 1:5, 1:6, 1:7, 1:8, 1:9, or 1:10 guest to colchicine.

The solid complexes can be physically distinguished from crystalline colchicine using a variety of analytical tools and characterization methods, such as, for example, Raman spectroscopy, IR spectroscopy (IR, FT-IR), X-ray powder diffraction (XRPD) crystallography, X-ray crystallography, neutron diffraction, Synchrotron radiation, solid state $^1$H-NMR spectroscopy, differential scanning calorimetry (DSC), Thermogravimetric analysis (TGA), Thermogravimetric/infrared analysis (TG-IR), melting point, and heats of fusion.

The colchicine solid complexes can be prepared using a variety of methods including crystallization, antisolvent precipitation, slow cooling of a solution of colchicine and guest, precipitation from a solution of colchicine and guest at a constant temperature (e.g., about room temperature, about 1.0 to about 4.0° C., about 0° C.), seeding solutions of colchicine and guest with optional cooling, slurrying, vapor diffusion, and the like.

Vapor diffusion process involves preparation of solutions of colchicine and a guest in a solvent system at ambient temperature. The solutions are placed into an open container and the container is placed in a sealed chamber containing an anti-solvent. The anti-solvent is miscible with the solvent system. The chamber is left undisturbed until solid formation occurs.

In one embodiment, a method of preparing colchicine malic acid co-crystal is by vapor diffusion of hexanes into an ethyl acetate solution containing equimolar amounts of colchicine and L-malic acid.

The solvent process generally involves preparing a solution or suspension of colchicine and guest in a solvent system followed by optional removal of the solvent. In the solution process, both colchicine and guest are completely dissolved in the solvent system, wherein in the suspension process, the colchicine or guest can remain partially undissolved.

"Solvent system" means a single or a combination of two or more solvents.

Suitable solvents for preparing the colchicine solid complex include those that do not adversely affect the stability of the colchicine, guest or solid complex, and are preferably inert. Suitable solvents may be organic, aqueous, or a mixture thereof. Suitable organic solvents may be aliphatic alcohols such as methanol (MeOH), ethanol (EtOH), n-propanol, isopropanol (IPA), n-butanol, tert-amyl alcohol (t-AmOH), tert-butyl alcohol, trifluoroethanol, and 2-ethoxyethanol, particularly lower alkyl ($C_1$-$C_6$) alcohols; ethers such as diethyl ether, tetrahydrofuran (THF), dioxane, methyl-tert-butyl ether, 1,2-dimethoxyethane (DME), and 2-methyl tetrahydrofuran; aliphatic ketones such as acetone, methyl ethyl ketone (MEK), and methyl isobutyl ketone; aliphatic carboxylic esters such as methyl acetate, ethyl acetate (EtOAc), and isopropyl acetate; aromatic hydrocarbons such as benzene, toluene, and xylene; aliphatic hydrocarbons such as hexanes; aliphatic nitriles such as acetonitrile (MeCN) and propionitrile; chlorinated hydrocarbons such as dichloromethane (DCM), chloroform, and carbon tetrachloride; aliphatic sulfoxides such as dimethyl sulfoxide (DMSO); amides such as dimethylformamide (DMF) and dimethylacetamide (DMA); organic acids such as acetic acid; N-methyl-2-pyrrolidone; pyridine; and the like, as well as mixtures comprising at least one of the foregoing organic solvents. Certain solvents can be used as an anti-solvent to induce crystal formation from solution.

Optionally, the solution, prior to any solids formation, can be filtered to remove any undissolved solids, solid impurities and the like prior to solid complex formation. Any filtration system and filtration techniques known in the art can be used.

In one embodiment, the solutions or suspensions can be seeded with the desired colchicine solid complex.

In one embodiment, the solutions or suspensions can be sonicated.

In one embodiment, a method of preparing colchicine oxalic acid co-crystal comprises crystallizing the co-crystal from a solution of acetonitrile and diethyl ether.

In another embodiment, a method of preparing colchicine para-toluenesulfonic acid co-crystal comprises crystallizing the co-crystal from a solution of tetrahydrofuran and hexanes.

In yet another embodiment, a method of preparing colchicine malic acid co-crystal comprises slurrying a combination of colchicine, L-malic acid, and ethyl acetate to form colchicine malic acid co-crystal.

In one embodiment, the solvent system of the solution or suspension of colchicine, guest, and solvent system is removed slowly or rapidly. Rapid removal of the solvent system can be achieved in less than a minute by processes such as spray drying. Slow removal of the solvent system can be achieved in a minute or greater using methods such as evaporation under reduced pressure or evaporation at atmospheric pressure. Removal of the solvent system can be achieved with optional heating.

In one embodiment, a colchicine malic acid solid complex is a co-crystal exhibiting XRPD peak positions at 6.0, 7.2, 8.5, 11.1, 13.1, 16.3, 16.7, 18.4, 19.9, 22.0, and 24.6±0.2 degrees 2-theta. In another embodiment, a colchicine malic acid solid complex is a co-crystal exhibiting the XRPD peak positions as in Table 1 below. In yet another embodiment, a colchicine malic acid solid complex is a co-crystal exhibiting an XRPD pattern which is substantially similar to FIG. 1. In another embodiment, a colchicine malic acid solid complex is a co-crystal exhibiting FT-Raman peaks at 2935, 1595, 1500, 1444, 1350, 1324, and 1287±4 $cm^{-1}$. In another embodiment, a colchicine malic acid solid complex is a co-crystal exhibiting FT-Raman peaks as in Table 3 below. In yet another embodiment, a colchicine malic acid solid complex is a co-crystal exhibiting a FT-Raman spectrum which is substantially similar to FIG. 2. In one embodiment, a colchicine malic acid solid complex is a co-crystal exhibiting an endotherm peak of about 70° C. by differential scanning calorimetry analysis. In one embodiment, a colchicine malic acid solid complex is a colchicine malic acid co-crystal having a ratio of about 1:1 malic acid:colchicine.

In one embodiment, a colchicine oxalic acid solid complex is a co-crystal exhibiting XRPD peak positions at 7.4, 9.2, 9.4, 10.8, 12.0, 12.3, 14.4, 15.9, 17.8, 18.9, 20.5, and 23.7±0.2 degrees 2-theta. In another embodiment, a colchicine oxalic acid solid complex is a co-crystal exhibiting the XRPD peak positions as in Table 4 below. In yet another embodiment, a colchicine oxalic acid solid complex is a co-crystal exhibiting an XRPD pattern which is substantially similar to FIG. 3. In another embodiment, a colchicine oxalic acid solid complex is a co-crystal exhibiting FT-Raman peaks at 2934, 1592, 1549, 1505, 1436, and 1401±4 $cm^{-1}$. In another embodiment, a colchicine oxalic acid solid complex is a co-crystal exhibiting FT-Raman peaks as in Table 6 below. In yet another embodiment, a colchicine oxalic acid solid complex is a co-crystal exhibiting a FT-Raman spectrum which is substantially similar to FIG. 4. In one embodiment, a colchicine oxalic acid solid complex is a co-crystal exhibiting an endotherm peak of about 144° C. by differential scanning calorimetry analysis. In one embodiment, a colchicine oxalic acid solid complex is a colchicine oxalic acid co-crystal having a ratio of about 1:2 oxalic acid:colchicine.

Figure 5:
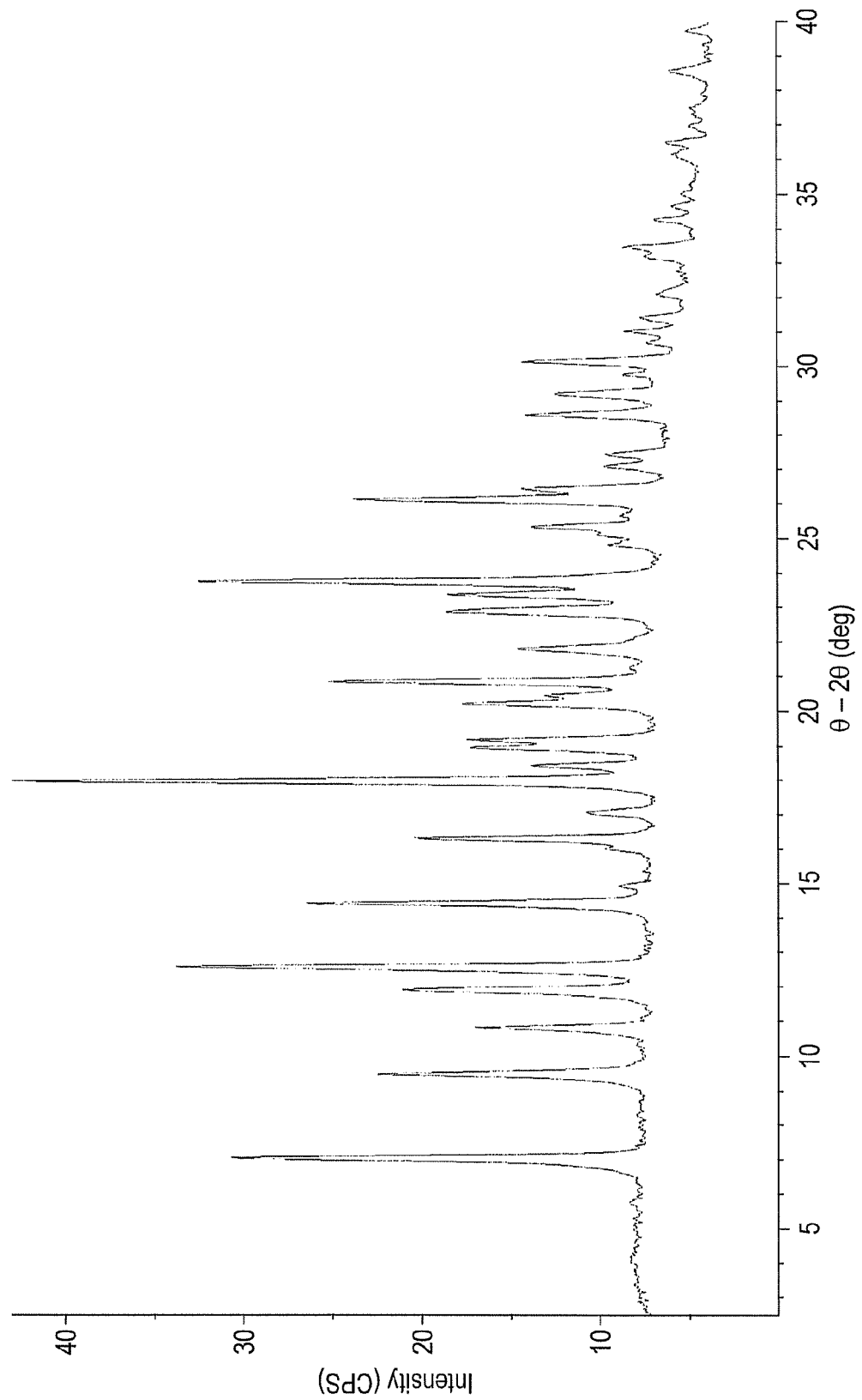
FIG. 5 illustrates an XRPD pattern of colchicine oxalic acid co-crystal, tetrahydrofuran solvate.

In another embodiment, a colchicine oxalic acid solid complex is a colchicine oxalic acid co-crystal, tetrahydrofuran solvate exhibiting an XRPD pattern which is substantially similar to FIG. 5. In one embodiment, a colchicine oxalic acid solid complex is a colchicine oxalic acid co-crystal, tetrahydrofuran solvate having a ratio of about 1:2:1 oxalic acid:colchicine:tetrahydrofuran.

In one embodiment, a colchicine para-toluenesulfonic acid solid complex is a co-crystal exhibiting XRPD peak positions at 6.6, 6.8, 9.6, 12.8, 14.3, 15.1, 17.1, 18.6, and 22.7±0.2 degrees 2-theta. In another embodiment, a colchicine para-toluenesulfonic acid solid complex is a co-crystal exhibiting the XRPD peak positions as in Table 8 below. In yet another embodiment, a colchicine para-toluenesulfonic acid solid complex is a co-crystal exhibiting an XRPD pattern which is substantially similar to FIG. 6. In another embodiment, a colchicine para-toluenesulfonic acid solid complex is a co-crystal exhibiting FT-Raman peaks at 1516, 1468, and 1322±4 cm$^{-1}$. In another embodiment, a colchicine para-toluenesulfonic acid solid complex is a co-crystal exhibiting FT-Raman peaks as in Table 10 below. In yet another embodiment, a colchicine para-toluenesulfonic acid solid complex is a co-crystal exhibiting a FT-Raman spectrum which is substantially similar to FIG. 7. In one embodiment, a colchicine para-toluenesulfonic acid solid complex is a co-crystal exhibiting an endotherm peak of about 198° C. by differential scanning calorimetry analysis. In one embodiment, a colchicine para-toluenesulfonic acid solid complex is a colchicine para-toluenesulfonic acid co-crystal having a ratio of about 1:1 para-toluenesulfonic acid:colchicine.

Also disclosed are pharmaceutical compositions comprising the colchicine solid complexes prepared herein.

Solid dosage forms for oral administration include, but are not limited to, capsules, tablets, powders, and granules. In such solid dosage forms, the solid complex may be admixed with one or more of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (1 solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, and combinations comprising one or more of the foregoing additives. For capsules and tablets, the dosage forms may also comprise buffering agents.

By "oral dosage form" is meant to include a unit dosage form for oral administration. An oral dosage form may optionally comprise a plurality of subunits such as, for example, microcapsules or microtablets. Multiple subunits may be packaged for administration in a single dose.

By "subunit" is meant to include a composition, mixture, particle, pellet, etc., that can provide an oral dosage form alone or when combined with other subunits.

The compositions can be immediate-release forms or controlled-release forms.

By "immediate-release" is meant a conventional or non-modified release in which greater then or equal to about 75% of the active agent is released within two hours of administration, specifically within one hour of administration.

By "controlled-release" is meant a dosage form in which the release of the active agent is controlled or modified over a period of time. Controlled can mean, for example, sustained-, delayed- or pulsed-release at a particular time. Alternatively, controlled can mean that the release of the active agent is extended for longer than it would be in an immediate-release dosage form, e.g., at least over several hours.

Dosage forms can be combination dosage forms having both immediate-release and controlled-release characteristics, for example, a combination of immediate-release pellets and controlled-release pellets. The immediate-release portion of a combination dosage form may be referred to as a loading dose.

Certain compositions described herein may be "coated". The coating may be a suitable coating, such as, a functional or a non-functional coating, or multiple functional or non-functional coatings. By "functional coating" is meant to include a coating that modifies the release properties of the total composition, for example, a sustained-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

Also disclosed are methods of treating a patient in need of colchicine therapy with a colchicine solid complex. The colchicine solid complexes disclosed herein and compositions prepared therefrom can be used in prevention or treatment of various diseases or conditions, including, for example, attacks of acute gouty arthritis and pain in attacks of acute gouty arthritis, chronic gout (prophylaxis), a cystic disease, for example polycystic kidney disease or cystic fibrosis, a lentiviral infection, demyelinating diseases of central or peripheral origin, multiple sclerosis, cancer, an inflammatory disorder such as rheumatoid arthritis, glaucoma, Dupuytren's contracture, idiopathic pulmonary fibrosis, primary amyloidosis, recurrent pericarditis, acute pericarditis, asthma, post-pericardiotomy syndrome, proliferative vitreoretinopathy, Behçet's disease, Familial Mediterranean fever, idiopathic thrombocytopenic purpura, primary biliary cirrhosis, and pyoderma gangrenosum, or in enhancing bone formation or bone mineral density.

The following examples further illustrate the invention but, of course, should not be construed as in any way limiting its scope.

EXAMPLES

The following experimental procedures are used unless stated otherwise.

X-Ray Powder Diffraction (XRPD) analyses are performed on a PANalytical X'Pert Pro diffractometer. The specimen is analyzed using Cu radiation produced using an Optix long fine-focus source. An elliptically graded multilayer mirror is used to focus the Cu Kα X-rays of the source through the specimen and onto the detector. The specimen is sandwiched between 3-micron thick films, analyzed in transmission geometry, and rotated to optimize orientation statistics. A beam-stop and helium purge are used to minimize the background generated by air scattering. Soller slits are used for the incident and diffracted beams to minimize axial divergence. Diffraction patterns are collected using a scanning position-sensitive detector (X'Celerator) located 240 mm from the specimen. Prior to the analysis a silicon specimen (NIST standard reference material 640c) was analyzed to verify the position of the silicon 111 peak. Peak lists were generated with PatternMatch 2.3.6.

Differential scanning calorimetry (DSC) analysis is carried out on a TA Instruments differential scanning calorimeter 2920; calibrated using indium reference. The sample is placed in a standard aluminum DSC pan with an uncrimped lid. The sample cell is equilibrated at 25° C. and heated under nitrogen purge at a rate of 10° C./minute up to a final temperature of 350° C.

Thermogravimetry (TG) analyses are carried out on a TA Instruments 2950 thermogravimetric analyzer. The calibration standards are nickel and Alumel™. Each sample is place in an aluminum sample pan and inserted into the TG furnace. Samples are started at ambient and then heated under a stream of nitrogen at a heating rate of 10° C./min, up to a final temperature of 350° C.

Fourier Transform Raman (FT-Raman) spectra are obtained using a FT-Raman 960 spectrometer (Thermo Nicolet) using an excitation wavelength of 1064 nm. Approximately 0.3 W or 0.5 W of Nd:YVO$_4$ laser power is used to irradiate the sample. The Raman spectra are measured with a germanium (Ge) detector. The samples are prepared for analysis by placing the material in a glass tube and positioning the tube in a gold-coated tube holder in the accessory. A total of 256 sample scans are collected from 3600-100 cm$^{-1}$ at a spectral resolution of 4 cm$^{-1}$, using Happ-Genzel apodization. Wavelength calibration is performed using sulfur. Data are analyzed and peak lists are generated by using Omnic v. 7.2 software.

Hot stage microscopy is performed using a Linkam hot stage (model FTIR 600) mounted on a Leica DM LP microscope. Samples are observed using a 20× objective (obj.) with cross polarizers (CP) and lambda (λ) compensator. Samples ae placed on a coverslip. A second coverslip is then placed over the sample. Each sample is visually observed as the stage is heated. Images are captured using a SPOT Insight™ color digital camera with SPOT Software v. 4.5.9. The hot stage is calibrated using USP melting point standards.

Dynamic vapor sorption/desorption (DVS) data are collected on a VTI SGA-100 Vapor Sorption Analyzer over a range of 5% to 95% relative humidity (RH) at 10% RH intervals under a nitrogen purge. Samples ae not dried prior to analysis. Equilibrium criteria used for analysis were less than 0.0100% weight change in 5 minutes, with a maximum equilibration time of 3 hours if the weight criterion was not met. Data are not corrected for the initial moisture content of the samples. Sodium chloride and polyvinypyrrolidine are used as calibration standards.

Example 1

Preparation of Colchicine Malic Acid Solid Complex: Co-Crystal

Colchicine malic acid co-crystal is prepared by a slurry experiment using ethyl acetate. Approximately 143 mg of colchicine and 146 mg of L-malic acid are placed into 5 mL of ethyl acetate. The mixture is left to slurry for one day. Excess ethyl acetate is then decanted and the solid is washed with approximately 10 mL of diethyl ether. The solid co-crystal is isolated by vacuum filtration. The isolated solids are analyzed using XRPD, FT-Raman, DSC, TGA, DVS, and $^1$H-NMR. The acid/colchicine ratio is approximately 1:1, and the material appears to be unsolvated.

The $^1$H-NMR spectrum is consistent with an unsolvated 1:1 malic acid cocrystal.

XRPD pattern of colchicine malic acid co-crystal is provided in FIG. 1 and a peak listing is provided in Table 1 below.

TABLE 1

| Position (°2θ) | I/I$_o$ |
|---|---|
| 6.0 | 14.75 |
| 7.2 | 100.00 |
| 8.5 | 16.63 |
| 11.1 | 28.60 |
| 12.0 | 15.73 |
| 13.1 | 66.83 |
| 13.4 | 20.46 |
| 14.0 | 12.10 |
| 14.4 | 15.09 |
| 16.3 | 42.47 |
| 16.7 | 37.47 |
| 16.9 | 21.98 |
| 17.7 | 16.60 |

TABLE 1-continued

| Position (°2θ) | I/I$_o$ |
|---|---|
| 18.4 | 51.14 |
| 19.0 | 10.28 |
| 19.9 | 27.99 |
| 20.6 | 16.70 |
| 22.0 | 64.35 |
| 23.3 | 26.34 |
| 23.6 | 27.18 |
| 24.1 | 14.31 |
| 24.6 | 47.95 |
| 26.3 | 12.84 |
| 26.8 | 14.25 |
| 27.6 | 19.69 |
| 27.9 | 14.21 |
| 28.9 | 13.44 |
| 29.4 | 15.66 |

The DSC curve of colchicine malic acid co-crystal exhibits an endotherm with an onset temperature at approximately 66° C. This event is confirmed by hotstage analysis as the melt. The TG curve exhibits a weight loss of approximately 2.8% up to 75° C., suggesting the material contains residual solvent.

The DVS data suggests the material is hygroscopic. The material exhibits a weight loss of approximately 1.5% upon equilibration at 5% RH, consistent with the thermal data above. A weight gain of approximately 22% is observed on the sorption step with no hysteresis upon desorption. Equilibrium weight is not achieved above 75% RH, indicating that higher weight gains may be possible.

A summary of the DSC, TG, Hotstage, DVS and $^1$H-NMR studies are provided in Table 2.

TABLE 2

| Analytical Technique | Results |
|---|---|
| DSC | Endo 70° C. |
| TG | 2.8% weight loss up to 75° C. |
| Hotstage | 24.6: birefringent with extinction |
| | 68.3: – |
| | 79.6: losing birefringence |
| | 82.0: melting |
| | 84.6: – |
| | 93.9: – |
| | 103.4: liquid flow |
| | 129.5: – |
| | 213.0: no decomposition observed |
| DVS | Sorption: |
| | 1.5% weight loss upon equilibration at 5% RH |
| | 6.2% weight gain from 5 to 75% RH |
| | 15.6% weight gain from 75 to 95% RH |
| | Desorption: |
| | 15.0% weight loss from 95 to 75% RH |
| | 9.6% weight loss from 75 to 5% RH |
| Post DVS XRPD | Colchicine malic acid co-crystal |
| $^1$H-NMR (MeOD) | Consistent with a 1:1 co-crystal |

Figure 2:
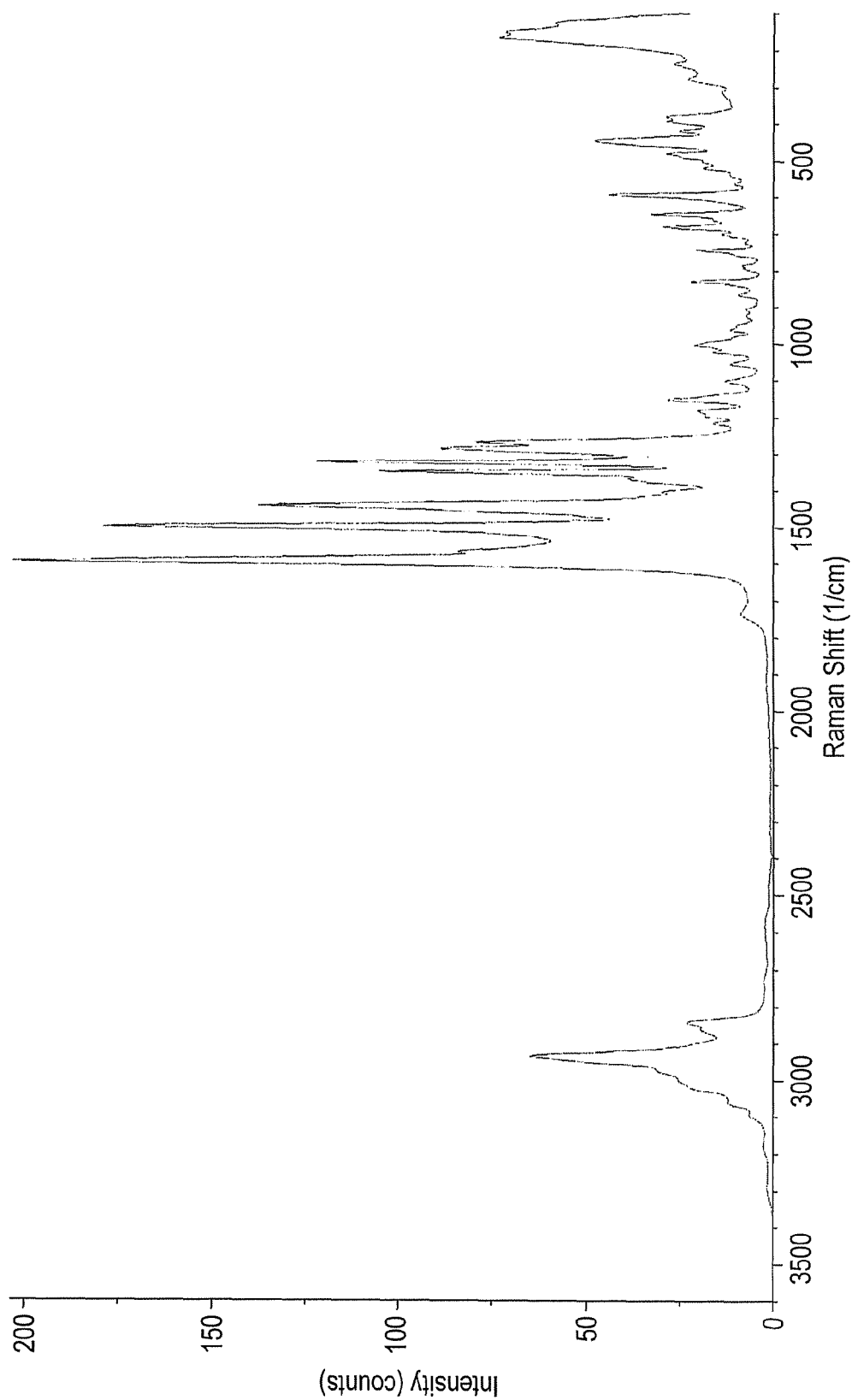
FIG. 2 illustrates a FT-Raman spectrum of colchicine malic acid co-crystal.

The Raman spectrum of colchicine malic acid co-crystal is shown in FIG. 2. The peak list is given in Table 3 below.

TABLE 3

| Position in Wavenumbers (cm$^{-1}$) | |
|---|---|
| 420 | 1054 |
| 448 | 1101 |
| 482 | 1151 |
| 521 | 1182 |

TABLE 3-continued

| Position in Wavenumbers (cm$^{-1}$) | |
|---|---|
| 562 | 1215 |
| 594 | 1269 |
| 646 | 1287 |
| 681 | 1324 |
| 701 | 1350 |
| 723 | 1368 |
| 743 | 1402 |
| 785 | 1444 |
| 793 | 1500 |
| 829 | 1566 |
| 864 | 1595 |
| 905 | 1732 |
| 920 | 2586 |
| 960 | 2844 |
| 1003 | 2935 |
| 1021 | 3179 |

The physical stability of colchicine malic acid co-crystal at 40° C./75% RH was investigated. The sample exhibits a net weight gain of approximately 5.4% after 4 days. The stressed sample is analyzed by XRPD and remains unchanged.

Example 2

Preparation of Colchicine Malic Acid Solid Complex: Single Crystal Study

Colchicine malic acid cocrystal is prepared by vapor diffusion of hexanes into an ethyl acetate solution containing equimolar amounts of free colchicine and L-malic acid. A 922 μL aliquot of an ethyl acetate stock solution of colchicine (217 mg, colchicine in 1000 μL) is combined with L-malic acid (122 μL) resulting in a clear solution. The vial is placed, uncapped, in a chamber containing approximately 3 mL hexanes. The chamber is sealed to allow for vapor diffusion. Crystals of colchicine malic acid co-crystal are obtained.

A piece of colchicine malic acid co-crystal having approximate dimensions of 0.44×0.40×0.33 mm, is mounted on a glass fiber in random orientation. Preliminary examination and data collection are performed with Mo K$_\alpha$ radiation (λ=0.71073 Å) on a Nonius KappaCCD diffractometer equipped with a graphite crystal, incident beam monochromator. Refinements are performed on an LINUX PC using SHELX. Cell constants and an orientation matrix for data collection are obtained from least-squares refinement using the setting angles of 12537 reflections in the range 3°<θ<27°. The refined mosaicity from Denzo/Scalepack is 0.52° indicating moderate crystal quality. The space group is determined by the program XPREP. From the systematic presence of the following conditions: hkl h+k+l=2n 00l l=4n, and from subsequent least-squares refinement, the space group is determined to be I 4$_1$ (no. 80). The data are collected to a maximum 2θ value of 54.95%, at a temperature of 150±1 K.

The tetragonal cell parameters and calculated volume are: a=20.7499(11), Å, b=20.7499(11), Å, c=15.2460(9), Å, α=90.00°, β=90.00°, γ=90.00°, V=6564.3(6) Å$^3$. The structure is determined to be an anhydrous crystal form of the malic acid co-crystal. The crystal structure is comprised of a three dimensional arrangement of colchicine molecules packed around columns of malic acid.

Example 3

Preparation of Colchicine Oxalic Acid Solid Complex: Co-Crystal

Colchicine oxalic acid co-crystal is prepared by either a cooling or ambient solution experiment involving acetonitrile and ether. Approximately 173 mg of colchicine and 38.8 mg of oxalic acid are placed into a solvent mixture containing approximately 2 mL of acetonitrile and 16 mL of diethyl ether. The material is left to crystallize in solution at room temperature. After 4 days, a solid is isolated by decanting the excess solvents. The oxalic acid co-crystal is isolated with an acid/colchicine ratio of 1:2. It appears to be unsolvated. The isolated solids are analyzed using XRPD, FT-Raman, DSC, TGA, DVS, and $^1$H-NMR.

Figure 3:
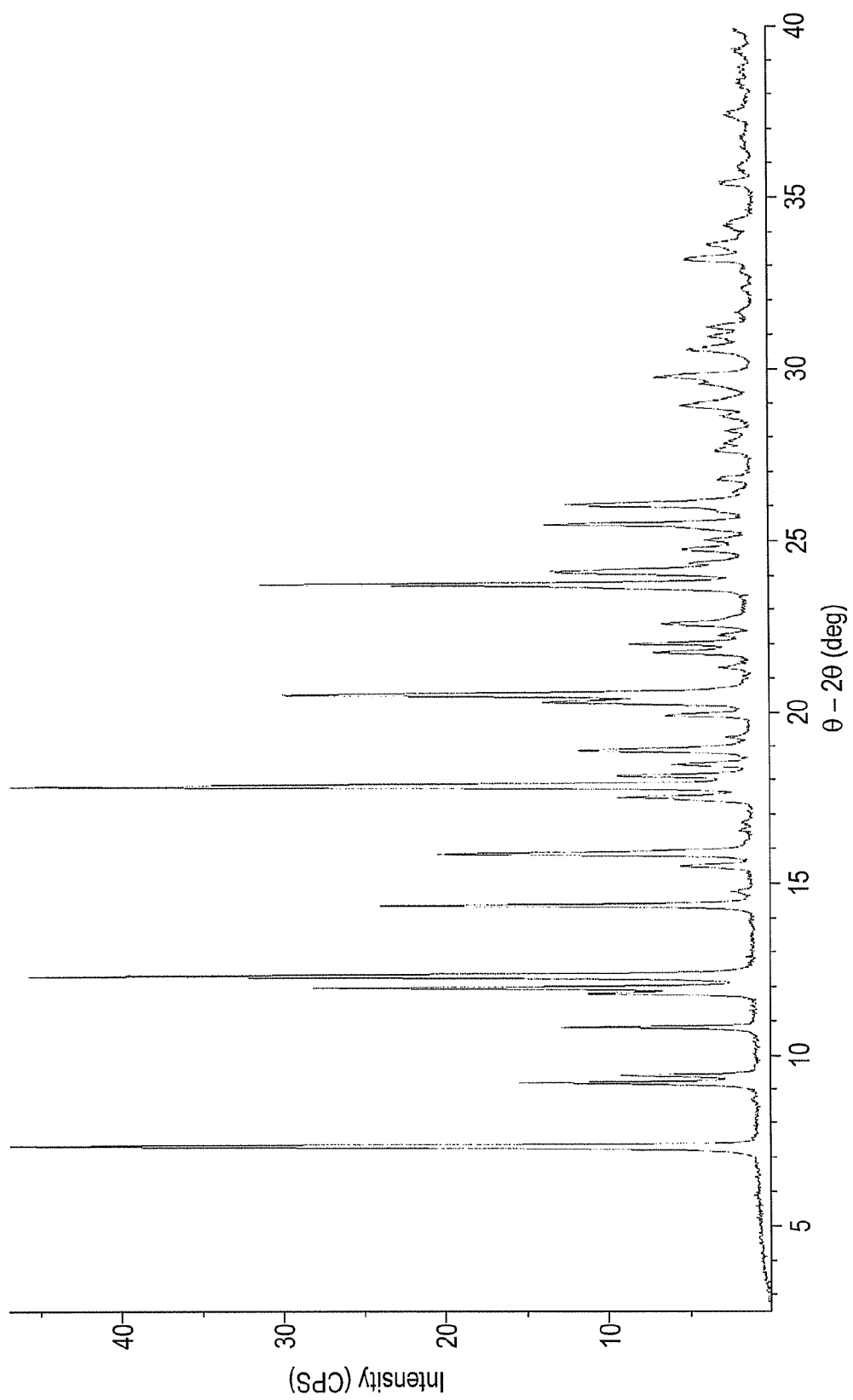
FIG. 3 illustrates an XRPD pattern of colchicine oxalic acid co-crystal.

XRPD pattern of colchicine oxalic acid co-crystal is provided in FIG. 3 and a peak listing is provided in Table 4 below.

TABLE 4

| Position (°2θ) | I/I$_o$ |
|---|---|
| 7.4 | 100.00 |
| 9.2 | 33.15 |
| 9.4 | 19.56 |
| 10.8 | 27.63 |
| 12.0 | 60.32 |
| 12.3 | 97.28 |
| 14.4 | 51.26 |
| 15.5 | 11.94 |
| 15.9 | 43.71 |
| 17.5 | 20.16 |
| 17.8 | 99.70 |
| 18.1 | 20.18 |
| 18.5 | 11.15 |
| 18.9 | 25.19 |
| 19.9 | 13.81 |
| 20.5 | 63.96 |
| 21.7 | 15.26 |
| 22.0 | 16.93 |
| 22.6 | 14.36 |
| 23.7 | 66.76 |
| 24.1 | 27.44 |
| 24.8 | 11.28 |
| 25.5 | 29.56 |
| 26.1 | 26.93 |
| 28.9 | 11.69 |
| 29.8 | 15.45 |

The DSC curve of colchicine oxalic acid co-crystal exhibits an endotherm with an onset temperature at approximately 131° C. This endotherm is confirmed as the melt by hotstage microscopy. Observed erratic endotherms above approximately 150° C. are indicative of decomposition. The TG curve exhibits a weight loss of approximately 1.7% up to 120° C., suggesting the material contains residual solvent (also observed by $^1$H-NMR).

The DVS data suggests the material is hygroscopic. The material exhibits a small weight loss of approximately 0.1% upon equilibration at 5% RH. The majority of the weight gain (~13%) during the sorption step is observed above 75% RH. Equilibrium weight is not achieved, indicating that higher weight gains may be possible. Significant hysteresis is observed upon desorption and the material deliquesces.

The $^1$H-NMR spectrum indicates that the structure of colchicine is intact. The stoichiometry of the acid/colchicine cannot be determined due to the absence of detectable protons in oxalic acid; however, elemental analysis indicates that the material has a ratio of 1:2 acid/colchicine.

A summary of the DSC, TG, Hotstage, DVS, $^1$H-NMR, and elemental analysis studies are provided in Table 5.

TABLE 5

| Analytical Technique | Results |
| --- | --- |
| DSC | Endo 144° C. |
| TG | 1.7% weight loss up to 120° C. |
| Hotstage | 26.9: birefringence with extinction |
| | 100.0: no changes |
| | 115.5: loss of birefringence, solid to liquid transition |
| | 118.5: continuing |
| | 121.2: continuing |
| | 126.0: continuing |
| | 131.4: continuing |
| | 135.5: slow flowing liquids |
| | 146.1: end of solid to liquid transition |
| DVS | Sorption: |
| | 0.1% weight loss upon equilibration at 5% RH |
| | 0.5% weight gain from 5 to 75% RH |
| | 12.9% weight gain from 75 to 95% RH |
| | Desorption: |
| | 15.2% weight loss from 95 to 5% RH |
| $^1$H-NMR (MeOD) | Consistent with structure of freebase |
| Elemental (non-GMP) | Consistent with 1:2 acid:colchicine cocrystal |
| | Theoretical: |
| | C: 62.15%, H: 5.90%, N: 3.15% |
| | Measured: |
| | C: 62.07%, H: 6.15%, N: 3.28% |

Figure 4:
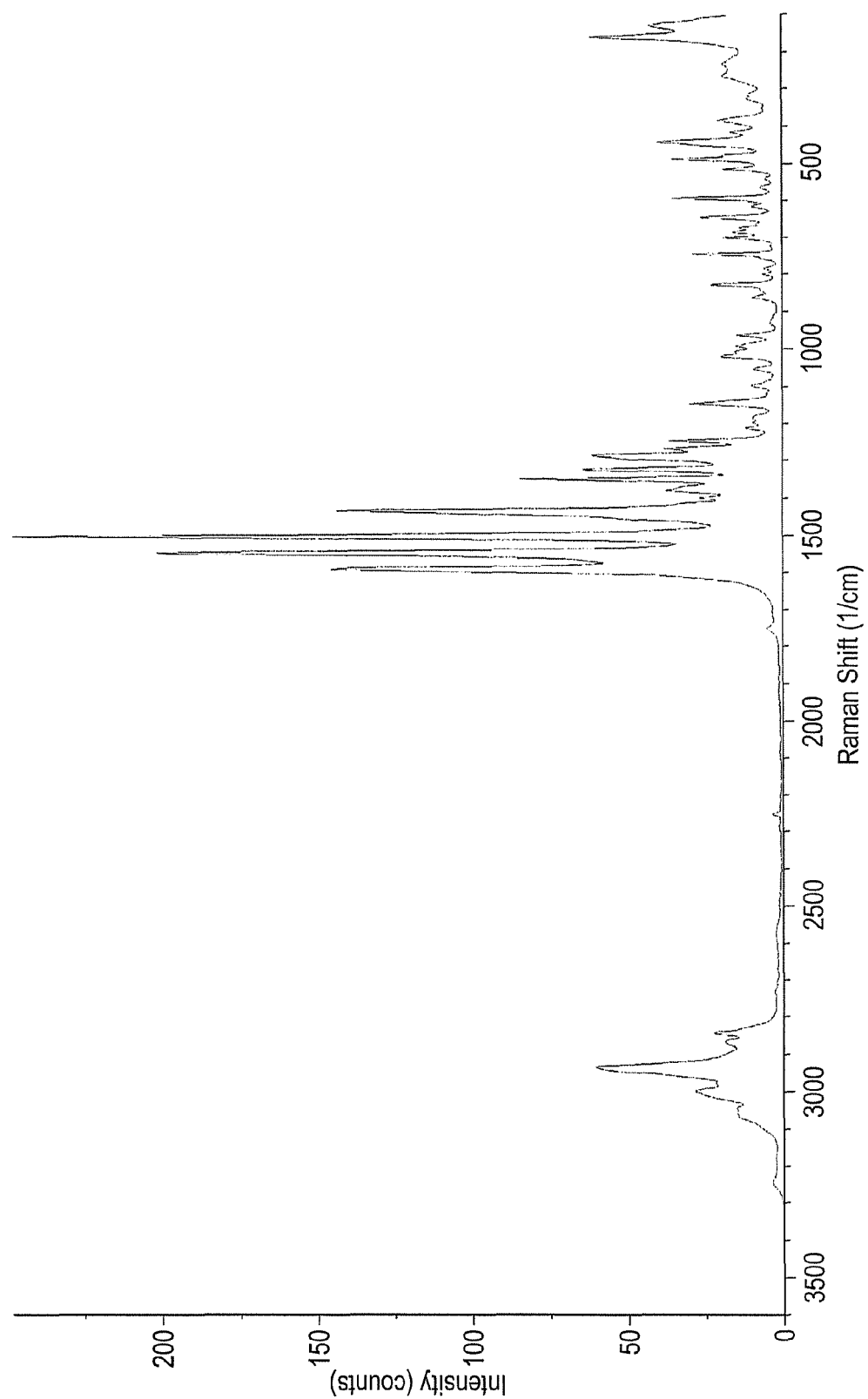
FIG. 4 illustrates a FT-Raman spectrum of colchicine oxalic acid co-crystal.

The Raman spectrum of colchicine oxalic acid co-crystal is shown in FIG. 4. The peak list is given in Table 6 below.

TABLE 6

| Position in Wavenumbers (cm$^{-1}$) | |
| --- | --- |
| 416 | 1148 |
| 443 | 1187 |
| 489 | 1198 |
| 515 | 1213 |
| 540 | 1247 |
| 563 | 1269 |
| 594 | 1287 |
| 615 | 1325 |
| 645 | 1350 |
| 674 | 1381 |
| 685 | 1401 |
| 700 | 1436 |
| 721 | 1505 |
| 744 | 1549 |
| 782 | 1592 |
| 797 | 1751 |
| 827 | 2252 |
| 861 | 2583 |
| 930 | 2842 |
| 964 | 2866 |
| 992 | 2934 |
| 1020 | 2998 |
| 1053 | 3045 |
| 1099 | 3242 |

The physical stability of colchicine oxalic acid co-crystal at 40° C./75% RH is investigated. The sample exhibits a net weight loss of approximately 6.7% after 4 days. The resulting sample is colchicine oxalic acid co-crystal, but minor disorder and shifting of the peaks is observed.

Example 4

Preparation of Colchicine Oxalic Acid Solid Complex: Co-Crystal, Tetrahydrofuran Solvate Colchicine oxalic acid co-crystal hemi-tetrahydrofuran solvate is isolated with an acid/colchicine ratio of 1:2. The material is prepared from an ambient solution experiment involving THF and hexanes.

The $^1$H-NMR spectrum indicates that the structure of colchicine is intact. The stoichiometry of the acid/colchicine cannot be determined due to the absence of detectable protons in oxalic acid. Elemental analysis (non-cGMP) indicates that the material has a ratio of 1:2 acid/colchicine and is also consistent with a hemi THF solvate. A summary of the $^1$H-NMR and elemental analyses is provided in Table 7 below.

TABLE 7

| Analytical Technique | Results |
| --- | --- |
| $^1$H-NMR (MeOD) | Consistent with structure, ~0.4 moles THF |
| Elemental (non-GMP) | Consistent with 1:2:1 acid/colchicine/THF solvated cocrystal |
| | Theoretical: |
| | C: 62.75%, H: 5.90%, N: 2.93% |
| | Measured: |
| | C: 62.64%, H: 6.36%, N: 2.91% |

An XRPD pattern of colchicine oxalic acid co-crystal tetrahydrofuran solvate is provided in FIG. 5.

Example 5

Preparation of Colchicine Para-Toluenesulfonic Acid Solid Complex: Co-Crystal Colchicine para-toluenesulfonic acid co-crystal is prepared from an ambient solution experiment involving THF and hexanes. Approximately 149 mg of colchicine and 70.9 mg of para-toluenesulfonic acid are placed into a solvent mixture containing approximately 5.6 mL of tetrahydrofuran and 1 mL of hexanes. The material is left to crystallize in solution at room temperature. After 1 day, colchicine para-toluenesulfonic acid co-crystal is isolated by vacuum filtration. The isolated solids are analyzed using XRPD, FT-Raman, DSC, TGA, DVS, and $^1$H-NMR. The acid/colchicine ratio is approximately 1:1, and the material appears to be unsolvated.

Figure 6:
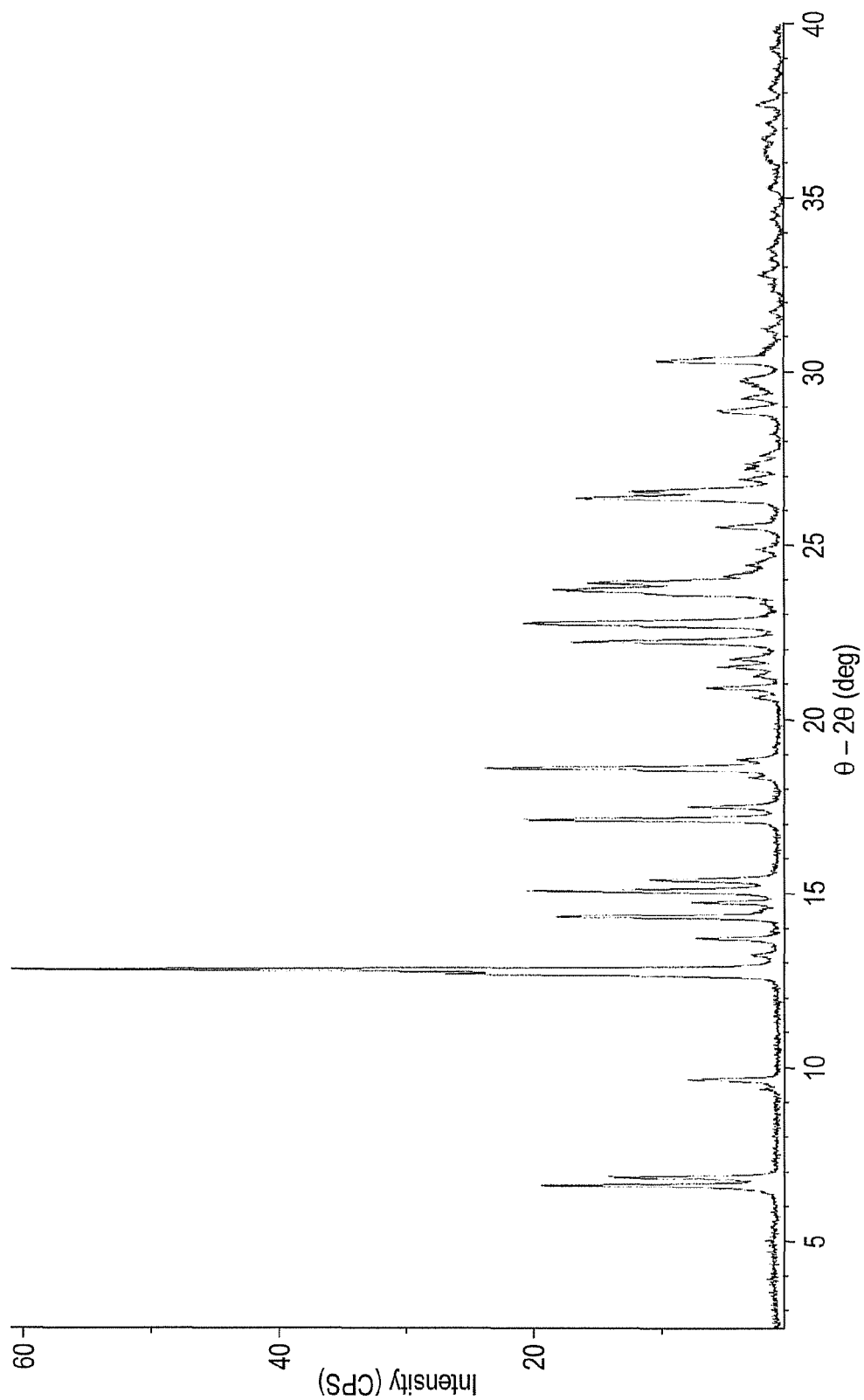
FIG. 6 illustrates an XRPD pattern of colchicine para-toluenesulfonic acid co-crystal.

XRPD pattern of colchicine para-toluenesulfonic acid co-crystal is provided in FIG. 6 and a peak listing is provided in Table 8 below.

TABLE 8

| Position (°2θ) | I/I$_o$ |
| --- | --- |
| 6.6 | 31.47 |
| 6.8 | 21.42 |
| 9.6 | 12.95 |
| 12.8 | 100.00 |
| 13.7 | 10.84 |
| 14.3 | 29.56 |
| 14.8 | 10.18 |
| 15.1 | 33.41 |
| 15.4 | 16.87 |
| 17.1 | 33.81 |
| 17.5 | 12.59 |
| 18.6 | 37.46 |
| 20.9 | 10.02 |
| 22.2 | 27.41 |
| 22.7 | 33.44 |
| 23.7 | 29.95 |
| 23.9 | 25.30 |
| 26.4 | 27.02 |

The DSC curve exhibits an endotherm with an onset temperature at approximately 198° C. Hotstage microscopy confirms this event as the melt, which occurs concurrently with decomposition. The TG curve exhibits a negligible weight loss of approximately 0.4% up to 175° C., suggesting the material is not solvated.

The DVS data suggests the material is not significantly hygroscopic. A weight gain of ~0.4% is observed during the sorption step. The material desorps slightly more weight upon desorption than was gained, with a net weight loss of ~0.01%. The resulting sample is colchicine para-toluenesulfonic acid co-crystal by XRPD.

The $^1$H-NMR spectrum is consistent with an unsolvated 1:1 para-toluenesulfonic acid cocrystal.

A summary of the DSC, TG, Hotstage, DVS, $^1$H-NMR, and elemental analysis studies are provided in Table 9.

TABLE 9

| Analytical Technique | Results |
| --- | --- |
| DSC | Endo 198° C. |
| TG | 0.4% weight loss up to 175° C. |
| Hotstage | 25.3: birefringent with extinction |
|  | 100.0: no change |
|  | 175.0: no change |
|  | 190.8: solid/liquid transition beginning |
|  | 196.7: solid/liquid transition done, decomposition observed |
|  | 32.4: no recrystallization |
| DVS | Sorption: |
|  | 0.01% weight loss upon equilibration at 5% RH |
|  | 0.4% weight gain from 5 to 95% RH |
|  | Desorption: |
|  | 0.5% weight loss from 95 to 5% RH |
| Post DVS XRPD | Colchicine toluenesulfonic acid co-crystal |
| $^1$H-NMR (MeOD) | Consistent with a 1:1 cocrystal |

The Raman spectrum of colchicine para-toluenesulfonic acid co-crystal is shown in FIG. 7. The peak list is given in Table 10 below.

TABLE 10

| Position in Wavenumbers (cm$^{-1}$) | |
| --- | --- |
| 441 | 987 |
| 459 | 1003 |
| 482 | 1019 |
| 506 | 1032 |
| 522 | 1053 |
| 535 | 1083 |
| 555 | 1095 |
| 580 | 1120 |
| 600 | 1148 |
| 618 | 1159 |
| 638 | 1177 |
| 664 | 1186 |
| 677 | 1213 |
| 703 | 1241 |
| 716 | 1273 |
| 728 | 1285 |
| 751 | 1301 |
| 785 | 1322 |
| 803 | 1349 |
| 833 | 1389 |
| 853 | 1441 |
| 863 | 1468 |
| 914 | 1494 |
| 949 | 1516 |

The physical stability of colchicine para-toluenesulfonic acid co-crystal at 40° C./75% RH is investigated. The sample exhibits a net weight gain of approximately 1.0% after 4 days. The resulting sample is analyzed by XRPD and is unchanged.

The terms "comprising", "having", "including", and "containing" are to be construed as open-ended terms (i.e., meaning "including, but not limited to"). The terms "a" and "an" do not denote a limitation of quantity, but rather denote the presence of at least one of the referenced item. The term "or" means "and/or". The endpoints of all ranges directed to the same component or property are inclusive and independently combinable.

Unless defined otherwise, technical and scientific terms used herein have the same meaning as is commonly understood by one of skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A solid complex, comprising:
   colchicine and malic acid,
   wherein the solid complex comprising colchicine and malic acid comprises a colchicine malic acid co-crystal exhibiting XRPD pattern comprising peak positions at 7.2, 11.1, 13.1, 16.3, 16.7, and 18.4±0.2 degrees 2-theta.

2. The solid complex of claim 1, wherein the XRPD pattern further comprises peak positions at 6.0, 8.5, 19.9, 22.0, and 24.6±0.2 degrees 2-theta.

3. The solid complex of claim 1, wherein the solid complex exhibits
   FT-Raman pattern comprising peaks at 2935, 1595, 1500, 1444, 1350, 1324, and 1287±4 cm$^{-1}$;
   an endotherm peak of about 70° C. by differential scanning calorimetry analysis; or both.

4. The solid complex of claim 1, wherein the solid complex has a ratio of about 1:1 malic acid:colchicine.

5. A solid complex, comprising:
   colchicine and oxalic acid,
   wherein the solid complex comprising colchicine and oxalic acid comprises a colchicine oxalic acid co-crystal exhibiting XRPD pattern comprising peak positions at 7.4, 9.2, 12.3, 14.4, 17.8, and 20.5±0.2 degrees 2-theta.

6. The solid complex of claim 5, wherein the XRPD pattern further comprises peak positions at 9.4, 10.8, 12.0, 15.9, 18.9, and 23.7±0.2 degrees 2-theta.

7. The solid complex of claim 5, wherein the solid complex exhibits
   FT-Raman pattern comprising peaks at 2934, 1592, 1549, 1505, 1436, and 1401±4 cm$^{-1}$;
   an endotherm peak of about 144° C. by differential scanning calorimetry analysis; or both.

8. The solid complex of claim 5, wherein the solid complex has a ratio of about 1:2 oxalic acid:colchicine.

9. A solid complex, comprising:
   colchicine and para-toluenesulfonic acid,
   wherein the solid complex comprising colchicine and para-toluenesulfonic acid comprises a colchicine para-toluenesulfonic acid co-crystal exhibiting XRPD pattern comprising peak positions at 6.6, 6.8, 12.8, 14.3, 15.1, 17.1, and 18.6±0.2 degrees 2-theta.

10. The solid complex of claim 9, wherein the XRPD pattern further comprises peak positions at 9.6 and 22.7±0.2 degrees 2-theta.

11. The solid complex of claim 9, wherein the solid complex exhibits
   FT-Raman pattern comprising peaks at 1516, 1468, and 1322±4 cm$^{-1}$;
   an endotherm peak of about 198° C. by differential scanning calorimetry analysis; or both.

12. The solid complex of claim 9, wherein the solid complex has a ratio of about 1:1 para-toluenesulfonic acid:colchicine.

13. A composition, comprising:
   the solid complex according to claim 1; and
   a pharmaceutically acceptable excipient.

14. The composition of claim 13, wherein the composition is a solid oral dosage formulation.

15. A composition, comprising:
   the solid complex according to claim 5; and
   a pharmaceutically acceptable excipient.

16. The composition of claim 15, wherein the composition is a solid oral dosage formulation.

17. A composition, comprising:
   the solid complex according to claim 9; and
   a pharmaceutically acceptable excipient.

18. The composition of claim 17, wherein the composition is a solid oral dosage formulation.

\* \* \* \* \*